(12) United States Patent
Akman et al.

(10) Patent No.: US 10,933,031 B2
(45) Date of Patent: Mar. 2, 2021

(54) USE OF GUAIACOL FOR THE PREVENTION AND TREATMENT OF GLYCOGEN STORAGE DISEASE

(71) Applicants: THE TRUSTEES OF COLUMBIA UNIVERSITY IN THE CITY OF NEW YORK, New York, NY (US); HADASIT MEDICAL RESEARCH SERVICES AND DEVELOPMENT LTD., Jerusalem (IL); RAMOT AT TEL-AVIV UNIVERSITY LTD., Tel Aviv (IL)

(72) Inventors: Hasan Orhan Akman, Haworth, NJ (US); Salvatore Dimauro, Bronx, NY (US); Or Kakhlon, Jerusalem (IL); Miguel Enrique Weil, Tel Aviv (IL)

(73) Assignees: The Trustees of Columbia University in the City of New York, New York, NY (US); Hadasit Medical Research Services and Development Ltd., Jerusalem (IL); Ramot at Tel-Aviv University, Ltd., Tel Aviv (IL)

( * ) Notice: Subject to any disclaimer, the term of this patent is extended or adjusted under 35 U.S.C. 154(b) by 0 days.

(21) Appl. No.: 16/068,251

(22) PCT Filed: Jan. 6, 2017

(86) PCT No.: PCT/US2017/012455
§ 371 (c)(1),
(2) Date: Jul. 5, 2018

(87) PCT Pub. No.: WO2017/120420
PCT Pub. Date: Jul. 13, 2017

(65) Prior Publication Data
US 2019/0015355 A1 Jan. 17, 2019

Related U.S. Application Data

(60) Provisional application No. 62/275,471, filed on Jan. 6, 2016.

(51) Int. Cl.
*A61K 31/085* (2006.01)
*A61K 31/05* (2006.01)
*A61P 3/08* (2006.01)
*A61K 9/00* (2006.01)
*G01N 33/53* (2006.01)

(52) U.S. Cl.
CPC .......... *A61K 31/085* (2013.01); *A61K 9/0053* (2013.01); *A61K 31/05* (2013.01); *A61P 3/08* (2018.01); *G01N 33/5308* (2013.01); *A01K 2217/075* (2013.01); *A01K 2227/105* (2013.01); *A01K 2267/0362* (2013.01); *G01N 2400/48* (2013.01); *G01N 2500/10* (2013.01)

(58) Field of Classification Search
USPC .......................................................... 514/718
See application file for complete search history.

(56) References Cited

U.S. PATENT DOCUMENTS

| 2007/0065524 A1 | 3/2007 | Wang |
| 2010/0184803 A1 | 7/2010 | Grammatopoulos et al. |
| 2010/0221225 A1 | 9/2010 | Byrne et al. |
| 2012/0082653 A1 | 4/2012 | Koeberl |

FOREIGN PATENT DOCUMENTS

| JP | H06199695 A | 7/1994 |
| WO | 2004093995 A2 | 11/2004 |
| WO | 2016090001 A1 | 6/2016 |
| WO | 2016161086 A1 | 10/2016 |

OTHER PUBLICATIONS

Hasan Ozen (World J. Gastroenterol. (2007) 14:2541-2533). (Year: 2007).*
Hasan O. Akman et al, "Fatal Infantile Cardiac Glycogenosis with Phosphorylase Kinase Deficiency and a Mutation in the 2-Subunit of AMP-Activated Protein Kinase", Pediatric Research, 2007, vol. 62 No. 4, pp. 499-504.
H. Orhan Akman et al, "Generation of a novel mouse model that recapitulates early and adult onset glycogenosis type IV", Human Molecular Genetics, 2011, vol. 20, No. 22, pp. 4430-4439.
H. Orhan Akman et al, "A novel mouse model that recapitulates adult-onset glycogenosis type 4", Human Molecular Genetics, 2015, vol. 24, No. 23, pp. 6801-6810.
Frederick M. Ausubel, "Chapter 26—Gene Silencing", Current Protocols in Molecular Biology, 2005.
Alexander A. Bachmanov et al, "Food Intake, Water Intake, and Drinking Spout Side Preference of 28 Mouse Strains", Behavior Genetics, Nov. 2002, vol. 32 No. 6, pp. 435-443.
Juan S. Bonifacino, "Chapter 15—Protein Trafficking", Cell Biology, 2005.
Christine Brideau et al, "Improved Statistical Methods for Hit Selection in High-Throughput Screening", Journal of Biomolecular Screening, Dec. 2003, vol. 8 No. 6, pp. 634-647.
Claudio Bruno et al, "Glycogen Branching Enzyme Deficiency in Adult Polyglucosan Body Disease", Annals of Neurology, Jan. 1993, vol. 33 No. 1, pp. 88-93.

(Continued)

*Primary Examiner* — Marcos L Sznaidman
(74) *Attorney, Agent, or Firm* — The Roy Gross Law Firm, LLC; Roy Gross

(57) ABSTRACT

The current invention is a method of preventing and treating certain diseases by preventing the synthesis and/or breakdown of glycogen by the administration of an agent, guaiacol. Diseases that can be prevented and treated by the administration of guaiacol include but are not limited to glycogen storage disease type IV (GSD-IV), adult polyglucosan body disease (APBD), and Lafora disease (LD). The invention also includes methods and tools for screening for agents that prevent and treat these diseases as well as basic research, specifically in the form of cells and cell lines that produce detectable polyglucosan.

10 Claims, 10 Drawing Sheets
Specification includes a Sequence Listing.

(56) References Cited

OTHER PUBLICATIONS

E.M. Chan et al, Progressive myoclonus epilepsy with polyglucosans (Lafora disease), Neurology, Aug. 10, 2004, vol. 63 No. 3, pp. 565-567.
John E. Coligan et al, "Preface", 2005, Current Protocols in Immunology.
Gail H. Deutsch et al, "Histologic resolution of pulmonary interstitial glycogenosis", Pediatric and Developmental Pathology, 2009, vol. 12 No. 6, pp. 475-480.
Ianzano L et al, "Lafora progressive Myoclonus Epilepsy mutation database-EPM2A and NHLRC1 (EPM2B) genes", Human Mutation, Oct. 2005, vol. 26 No. 4 p. 397.
Barbara Illingworth et al, "Structure of glycogens and amylopectins. I. Enzymatic determination of chain length.", Journal of Biological Chemistry, Dec. 1952, vol. 199 No. 2, pp. 631-640.
Alexander V. Skurat et al, "GNIP, a novel protein that binds and activates glycogenin, the self-glucosylating initiator of glycogen biosynthesis", Journal of Biological Chemistry, May 2002, vol. 277 No. 22, pp. 19331-19338.
Marianne Suter et al, "Dissecting the role of 5'-AMP for allosteric stimulation, activation, and deactivation of AMP-activated protein kinase", Journal of Biological Chemistry, Oct. 2006, vol. 281 No. 43, pp. 32207-32216.
Sixin Jiang, et al, "Starch binding domain-containing protein 1/genethonin 1 is a novel participant in glycogen metabolism", Journal of Biological Chemistry, Nov. 2010, vol. 285 No. 45, pp. 34960-34971.
Edoardo Malfatti et al, "A new muscle glycogen storage disease associated with glycogenin-1 deficiency", Annals of Neurology, Dec. 2014, vol. 76 No. 6, pp. 891-898.
Merce Márquez et al, "Characterisation of Lafora-like bodies and other polyglucosan bodies in two aged dogs with neurological disease", Journal of Veterinary Science, Feb. 2010, vol. 183 No. 2, pp. 222-225.
He Meng et al, "Localization of blood proteins thrombospondin1 and ADAMTS13 to cerebral corpora amylacea", Neuropathology, Dec. 2009, vol. 29 No. 6, pp. 664-671.
Berge A. Minassian et al, "Mutations in a gene encoding a novel protein tyrosine phosphatase cause progressive myoclonus epilepsy", Nature Genetics, Oct. 1998, vol. 20 No. 2, pp. 171-174.

Fanny Mochel et al, "Adult polyglucosan body disease: Natural History and Key Magnetic Resonance Imaging Findings", Annals of Neurology, Sep. 2012, vol. 72 No. 3, pp. 433-441.
Johanna Nilsson et al, "Polyglucosan body myopathy caused by defective ubiquitin ligase RBCK1", Annals of Neurology, Dec. 2013, vol. 74 No. 6, pp. 914-919.
Bartholomew A. Pederson et al, "Abnormal cardiac development in the absence of heart glycogen", Molecular and Cellular Biology, Aug. 2004, vol. 24 No. 16, pp. 7179-7187.
Sumana Santra et al, "Ketogenic treatment reduces deleted mitochondrial DNAs in cultured human cells", Annals of Neurology, Nov. 2004, vol. 56 No. 5, pp. 662-669.
David Stapleton et al, "Mammalian AMP-activated protein kinase subfamily", Journal of Biological Chemistry, Jan. 1996 vol. 271 No. 2, pp. 611-614.
Todaro GJ et al, "Quantitative studies of the growth of mouse embryo cells in culture and their development into established lines", Journal of Cell Biology, May 1963 May vol. 17, pp. 299-313.
Julie Turnbull et al, "PTG depletion removes Lafora bodies and rescues the fatal epilepsy of Lafora disease", PLOS Genetics, Apr. 2011, vol. 7 No. 4.
X. Wu et al, "Characterization of Gac1p, a regulatory subunit of protein phosphatase type I involved in glycogen accumulation in *Saccharomyces cerevisiae*", Molecular Genetics and Genomics, Jun. 2001, vol. 265, No. 4, pp. 622-635.
Lanmin Zhai et al, "Structure and chromosomal localization of the human glycogenin-2 gene GYG2", Gene, 2000, vol. 242, pp. 229-235.
Andersen DH. "Familial cirrhosis of the liver with storage of abnormal glycogen", Laboratory Investigation, Jan.-Feb. 1956, vol. 5 No. 1, pp. 11-20.
Bruno et al., Neuromuscular forms of glycogen branching enzyme deficiency, Acta Myologica, 2007; XXXVI; p. 75-78.
Fayaz et al., Finding Needles in a Haystack: Application of Network Analysis and Target Enrichment Studies for the Identification of Potential Anti-Diabetic Phytochemicals, PLOS ONE, Nov. 2014, vol. 9, Issue 11, e112911.
The 8th Annual Conference of The Israeli Society of Gene & Cell Therapy—Apr. 22, 2013, Hadassah Hebrew University Medical Center—Jerusalem, Israel, Human Gene Therapy, vol. 24, No. 3, Mar. 1, 2013, pp. A1-A15, XP055072285.

* cited by examiner

Figure 1
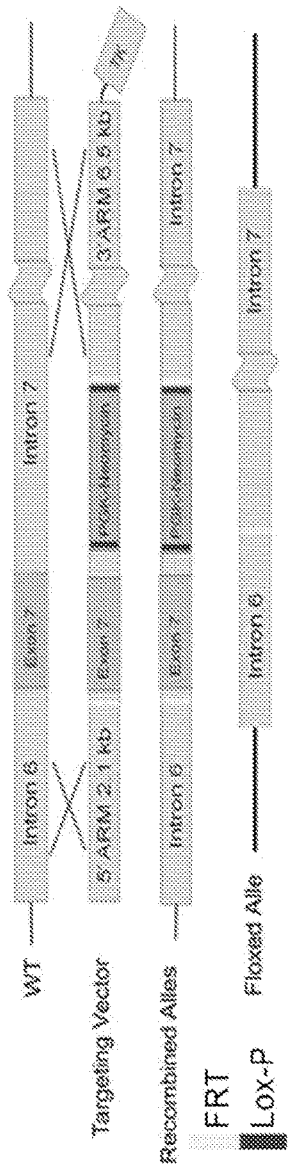
Figure 1A
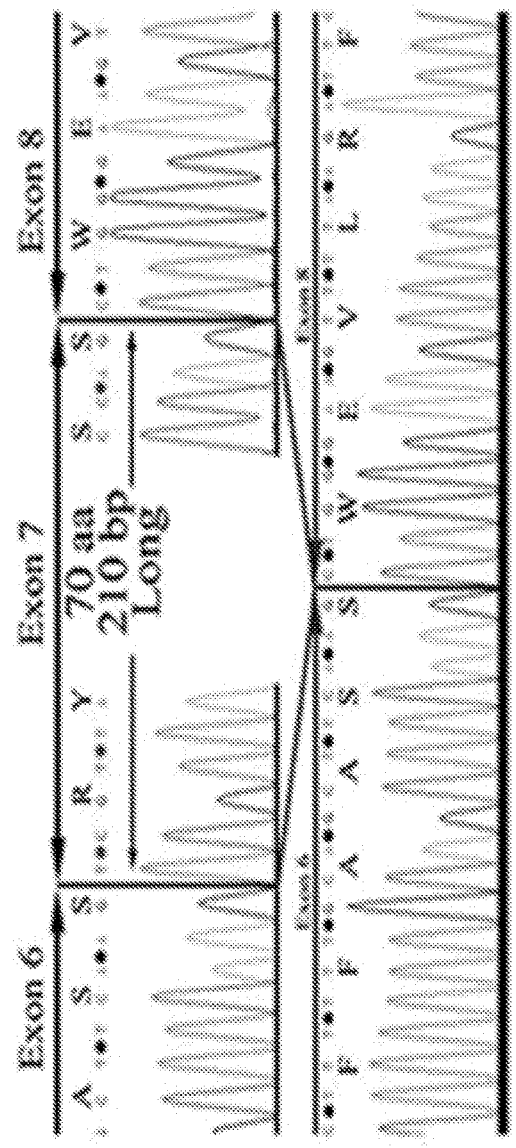
Figure 1B

Figure 2A
Figure 2B
Figure 2C
Figure 2D
Figure 2E
Figure 2F
Figure 2G
Figure 2H
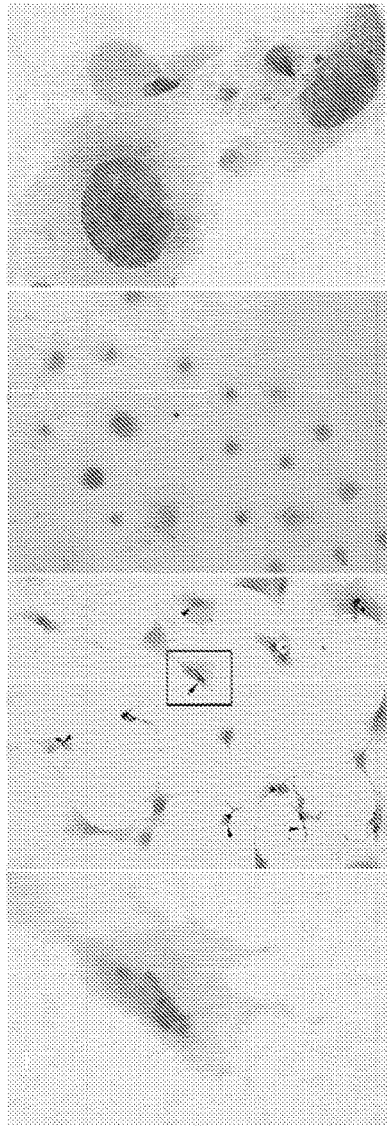
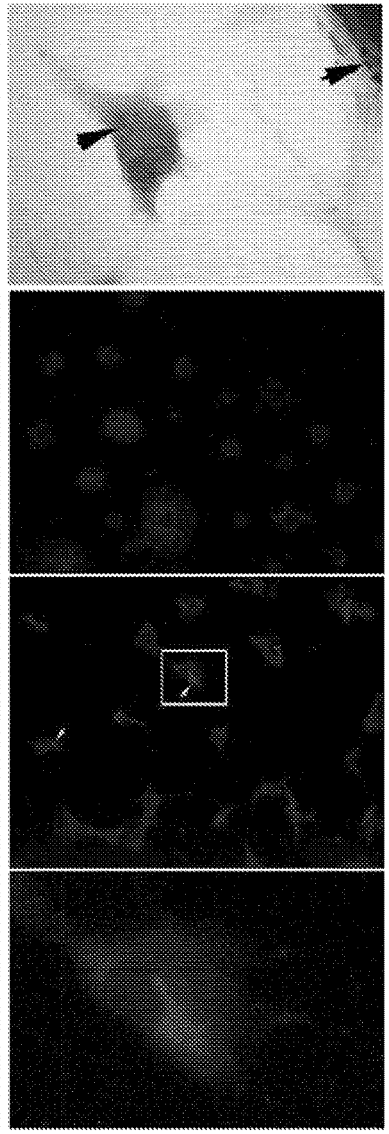
Figure 2

USE OF GUAIACOL FOR THE PREVENTION AND TREATMENT OF GLYCOGEN STORAGE DISEASE

CROSS-REFERENCE TO RELATED APPLICATIONS

This application is a National Phase of PCT Patent Application No. PCT/US2017/012455 having International filing date of Jan. 6, 2017, which claims the benefit of priority to U.S. Patent Application Ser. No. 62/275,471, filed Jan. 6, 2016. The contents of the above applications are all incorporated by reference as if fully set forth herein in their entirety.

FIELD OF THE INVENTION

This invention is in the field of preventing and treating certain diseases or disorders characterized by the accumulation of glycogen and/or polyglucosan by preventing the synthesis and/or breakdown of glycogen, as well as in the field of screening for agents that prevent and treat these diseases.

BACKGROUND OF THE INVENTION

Glycogen is a branched polysaccharide with a molecular weight of nine to ten million daltons. The average glycogen molecule contains about 55,000 glucose residues linked by $\alpha$-1,4 (92%) and $\alpha$-1,6 (8%) glycosidic bonds. The synthesis of glycogen is catalyzed by two enzymes: (i) glycogen synthase, which "strings" glucose to form linear chains; and (ii) the glycogen branching enzyme (GBE), which attaches a new short branch of glucose units to a linear chain in an $\alpha$-1,6 glycosidic bond. Glycogen is stored primarily in liver and muscle, where it represents an energy reserve that can be quickly mobilized. The most common disorder of glycogen metabolism is seen in diabetes, in which abnormal amount of insulin or abnormal insulin response result in accumulation or depletion of liver glycogen. Although glycogen synthesis and breakdown have been studied for decades, their control is not completely understood.

Hereditary glycogen storage diseases have been associated with various enzyme deficiencies. For example, glycogen storage disease type IV (GSD-IV) is an autosomal recessive disorder caused by glycogen branching enzyme deficiency. One form of GSD, adult polyglucosan-body disease (APBD), is characterized by onset after age 50 of progressive pyramidal paraparesis, distal sensory deficits, neurogenic bladder, ambulation loss, and premature death due to complications of myelopathy and peripheral neuropathy (Klein 2009; Mochel et al. 2012). The neuropathological hallmark of APBD, like all GSDs, is glycogen accumulation, but in the case of GSD-IV, glycogen is poorly branched, and is called polyglucosan (PG). PG precipitates in the cell forming large bodies called polyglucosan bodies (PGB), which aggregate in the central nervous system (CNS) and peripheral nervous system (PNS). In neurons, PGBs are principally in axons, often appearing to fill the axons. There is no current treatment available for APBD or any GSD-IV disease.

APBD is allelic to GSD-IV. Classical GSD-IV patients have profound GBE deficiency and die in childhood of liver failure with massive hepatic and extrahepatic polyglucosan accumulations. Individuals with complete deficiency usually die prenatally (Andersen 1956). Most APBD patients are of Ashkenazi Jewish descent, and 70% are homozygous for the NM_000158:c.986A>C/p.Y329S GBE1 mutation. There are no known Ashkenazi Jewish APBD patients who do not carry at least one copy of the p.Y329S mutation.

Although the pathogenicity of PGB is not well understood, similar PG aggregates are also found in Lafora disease (LD), partial glycogenin deficiency and in the normal aging brain (Marquez et al. 2010; Meng et al. 2009), despite the normal GBE activity in these conditions. Elimination of PG in Lafora mouse models by reducing glycogen synthase activity was shown to ameliorate symptoms (Turnbull et al. 2011).

While LD and GSD-IV share the same histopathological feature of diastase-resistant PAS-positive polyglucosan bodies (PGB), the two diseases are caused by mutations in different genes and have very different clinical pictures. LD is an autosomal recessive disorder presenting in teenage years with progressive myoclonic epilepsy that leads to death within a decade of onset. The pathogenesis of LD does not directly involve glycolytic enzymes but regulatory enzymes that may indirectly affect glycolytic enzymes (Ianzano et al. 2005). Two genes causing Lafora disease, EPM2A and NHLRC1 (EPM2B), have been identified (Chan et al. 2004; Minassian et al. 1998). The EPM2A gene product, laforin, is a protein tyrosine phosphatase with a carbohydrate-binding domain. NHLRC1 encodes the protein malin, an E3 ubiquitin ligase that acts on laforin. In LD, abnormal signal transduction or control of protein degradation via ubiquitinylation seems to alter the collaborative work of GS and GBE. Recently two other genes have been described by this laboratory and collaborators. One is another E3 ubiquitin ligase responsible for PGB in muscle and heart only, again different than both Lafora and GSD-IV (Nilsson et al. 2013). The second results in a reduced (but not deficient) amount of muscle glycogenin described in a select group of patients from the island of Sardinia (Malfatti et al 2014).

Thus, there is still much unknown about the mechanisms that lead to polyglucosan formation in LD, GSD-IV, and other glycogenoses (Deutsch and Young 2000; Tonin et al. 1992). Given the late onset and residual GBE activity of APBD, it would be important to devise strategies aimed at boosting, if not restoring, glycogen branching activity or aimed at disposing of the accumulated polyglucosan.

SUMMARY OF THE INVENTION

The current invention is a method of preventing and/or treating a disease or disorder characterized by accumulation of glycogen and/or polyglucosan, by administering to a subject in need thereof a therapeutically effective amount of an agent that reduces and/or decreases the accumulation of glycogen and/or polyglucosan. In one embodiment, the polyglucosan is accumulated in polyglucosan bodies (PGBs). In one embodiment, the agent is a small molecule inhibitor. In a further embodiment, the small molecule inhibitor is guaiacol.

In one aspect of the invention, all glycogen storage diseases, those currently known and those later discovered, can be prevented and/or treated by administration of guaiacol including, Types I-IX. In particular, adult polyglucosan body disease or APBD, can be prevented and/or treated by the administration of guaiacol. Additionally, Lafora disease or LD can also be prevented and/or treated by the administration of guaiacol.

In a further aspect of the present invention, diseases and disorders marked by an abnormal accumulation of PGBs can also be prevented and/or treated by the administration of guaiacol.

In a further aspect of the invention, glycogen storage diseases and disorders can be prevented and/or treated by the administration of guaiacol.

In a further aspect of the invention, diabetes can be prevented and/or treated by the administration of guaiacol.

In one embodiment, the subject is a mammal and in the most preferred embodiment, the mammal is a human.

In one embodiment, the administration is oral and the dosage is from about 22.5 to 720 milligram of guaiacol per kilogram of the subject.

Administration of the guaiacol can be once daily, twice daily, three times daily, four times daily, five times daily, up to six times daily, preferably at regular intervals.

Administration of the guaiacol should begin as soon as the disease or disorder characterized by accumulation of glycogen and/or polyglucosan is suspected and continue throughout the life of the patient. Tests for the diagnosis of such disorders, including genetic testing, are known in the art.

The present invention also provides for methods and tools for drug design, testing of agents, and tools for basic research into the causes and etiology of glycogen storage disease, including APBD, and for diseases and disorders characterized by the abnormal accumulation of polyglucosan and PGBs.

One embodiment is a high throughput assay for testing and design of agents for the prevention and/or treatment of glycogen storage disease, including APBD, and for diseases and disorders characterized by the abnormal accumulation of polyglucosan and PGBs. In particular, the high throughput assay utilizes cells originating from a mouse model for GBE deficiency. In one embodiment, these cells are mouse embryonic cells. In a further embodiment, the cells are mouse embryonic fibroblasts (MEF). In a further embodiment, the cells accumulate polyglucosan (PG). In a further embodiment, the polyglucosan is in the form of polyglucosan bodies (PGB). In a further embodiment, the polyglucosan or polyglucosan bodies are detectable and/or measurable.

The present invention also provides a mouse model for APBD, wherein the GBE enzyme activity is decreased enough to allow for polyglucosan accumulation and/or the mouse is compound heterozygous for the GBE1 mutation.

The present invention also provides for cells originating from this mouse model, wherein the GBE enzyme activity is decreased enough to allow for polyglucosan accumulation and/or the mouse is compound heterozygous for the GBE1 mutation. In one embodiment these cells are embryonic cells. In a further embodiment, the cells are embryonic fibroblasts. In a further embodiment, the cells accumulate polyglucosan (PG). In a further embodiment, the polyglucosan is in the form of polyglucosan bodies (PGB). In a further embodiment, the polyglucosan or polyglucosan bodies are detectable and/or measurable.

The present invention also provides for a cell line of mouse embryonic fibroblasts comprising cells that accumulate polyglucosan (PG). In a further embodiment, the polyglucosan is in the form of polyglucosan bodies (PGB). In a further embodiment, the polyglucosan or polyglucosan bodies are detectable and/or measurable.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

FIGS. 1A-1B show the gene targeting and molecular characterization of a GBE1 deficient mouse model. FIG. 1A is the partial map of the Gbe1 locus and the targeting vector containing FRT sites flanking exon 7, before and after homologous recombination in ES cells. Crossing Gbe1$^{+}$/neo mice with ROSA 26-flpe mice excises exon 7 from one allele of the Gbe1 gene by Flpe recombinase. Subsequent breeding of heterozygous mice Gbe1$^{+/-}$ creates a Gbe1 knockout mouse (Gbe1$^{-/-}$). FIG. 1B are electropherograms showing the results of RT-PCR and the sequence analysis of the mRNA extracted from neonatal muscle tissue of exons 6 to 8 of wild type (top) and Gbe1$^{-/-}$ (bottom) cDNA FIGS. 2A-2H show the diastase resistant PAS positive PGB accumulations in Gbe1$^{neo/-}$ MEF are detectable by light microscopy as well as fluorescent microscopy. FIG. 2A shows Gbe1$^{+/+}$ cells do not have PAS positive staining in the cytosol. FIG. 2B shows Gbe1$^{neo/-}$ fibroblasts accumulate PGB indicated by arrow heads. FIGS. 2C and 2D show PAS stained control MEF with lower magnification (FIG. 2C) and fluorescent image of the same field (FIG. 2D), using the same imaging technique used to detect PGB in Gbe1$^{neo/-}$ MEF in FIGS. 2E and 2F, respectively. Arrow heads indicate the PGB in FIGS. 2E and 2F. Digital Magnification of the squared fields in FIGS. 2E and 2F are showing large round PGBs in FIGS. 2G and 2H.

FIG. 3A shows diastase treated PAS stained MEF cultures treated with 10 μM guaiacol decreased PAS stained granules in the cytosol indicated by the arrow heads. FIG. 3B shows a decrease of glycogen content in MEF (n=3). FIG. 3C is a graph showing the results of relative glycogen content of cells grown in cobalt supplemented media after 3 days of guaiacol treatment at concentrations indicated on horizontal axis.

DETAILED DESCRIPTION OF THE INVENTION

Definitions

Figures 3, 3A, 3B:
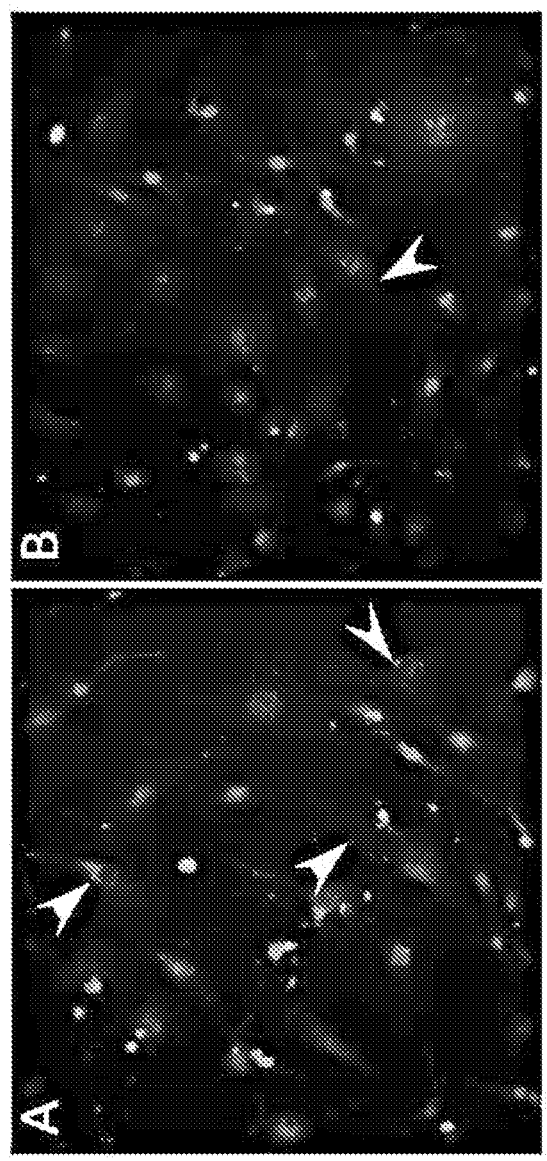
FIGS. 3A-3C show guaiacol decreases glycogen synthesis.
Figure 3C:
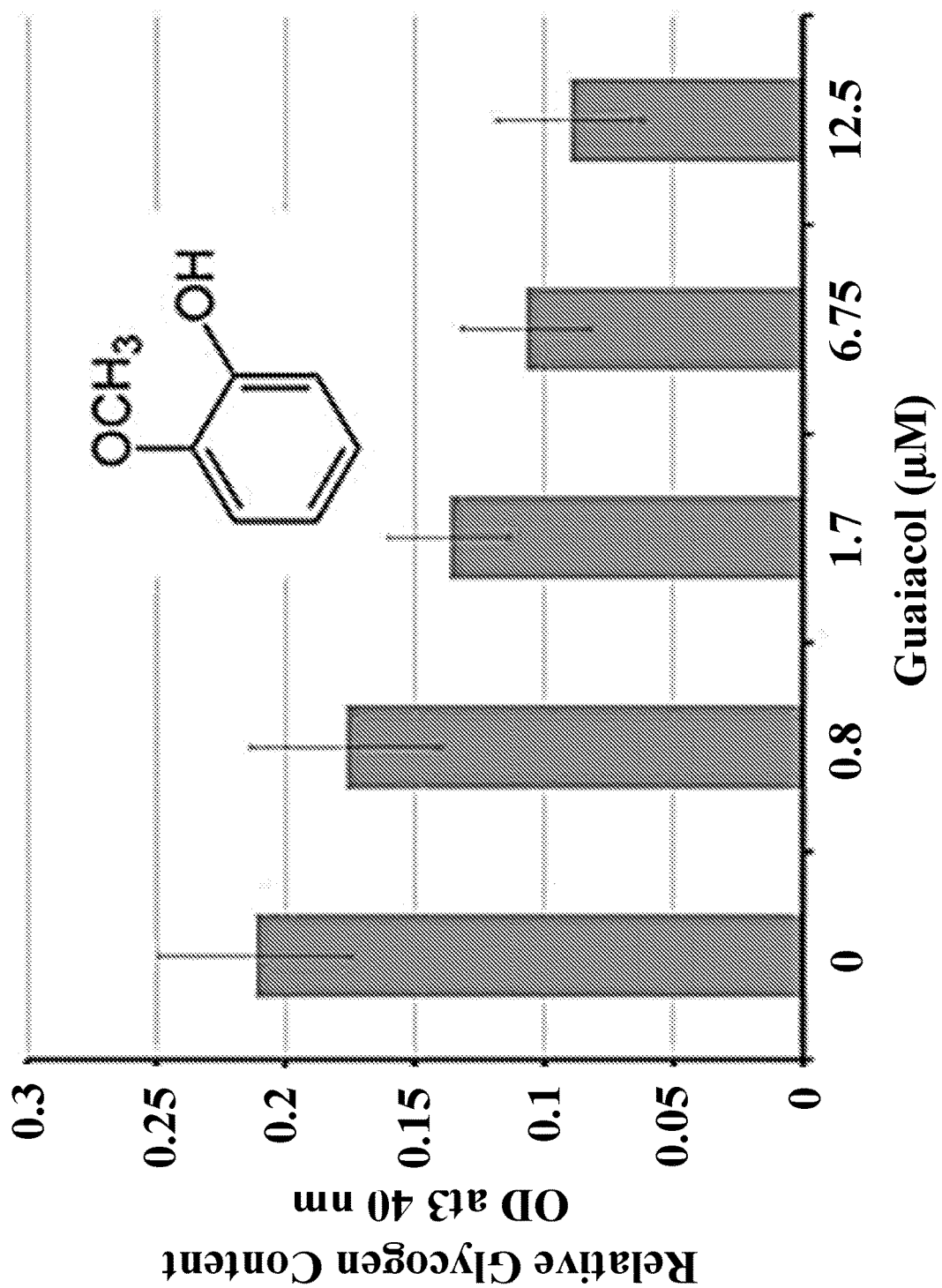

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

"Adult polyglucosan body disease" or "APBD" will be used interchangeably and is a glycogen storage disease characterized by a constellation of progressive and debilitating symptoms, including progressive pyramidal paraparesis, distal sensory deficits, neurogenic bladder, ambulation loss, and premature death due to complications of myelopathy and peripheral neuropathy.

As used herein, the term "polyglucosan bodies" or "PGBs" means accumulations of aggregated, poorly branched insoluble glycogen, polyglucosan or PG, in the central nervous system (CNS) and peripheral nervous system (PNS), which are the neuropathological hallmark of APBD. In neurons, PGB are principally in axons, often appearing to fill the axons.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having or being at risk of developing adult polyglucosan body disease (APBD), a glycogen storage disease (GSD) including types I-IX, Lafora disease (LD), a disease characterized by abnormal accumulation of PGBs, and/or a disease or disorder characterized by abnormal accumulation of glycogen. The subject can also be known or suspected of having or being at risk for developing diabetes.

A subject in need of treatment would be one that has already been diagnosed with APBD, a GSD or LD or a disease or disorder characterized by the abnormal accumulation of PGBs and/or glycogen. A subject in need of prevention would be one with risk factors of APBD, GSD or LD or a disease or disorder characterized by the abnormal accumulation of PGBs and/or glycogen or of Ashkenazi Jewish descent.

The terms "screen" and "screening" and the like as used herein means to test an agent to determine if it has a particular action or efficacy.

The terms "identification", "identify", "identifying" and the like as used herein means to recognize an agent as being effective for a particular use.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

In accordance with the present invention, there may be numerous tools and techniques within the skill of the art, such as those commonly used in molecular immunology, cellular immunology, pharmacology, and microbiology. See, e.g., Sambrook et al. (2001) *Molecular Cloning: A Laboratory Manual,* 3rd ed. Cold Spring Harbor Laboratory Press: Cold Spring Harbor, N.Y.; Ausubel et al. eds. (2005) *Current Protocols in Molecular Biology,* John Wiley and Sons, Inc.: Hoboken, N.J.; Bonifacino et al. eds. (2005) *Current Protocols in Cell Biology,* John Wiley and Sons, Inc.: Hoboken, N.J.; Coligan et al. eds. (2005) *Current Protocols in Immunology,* John Wiley and Sons, Inc.: Hoboken, N.J.; Coico et al. eds. (2005) *Current Protocols in Microbiology,* John Wiley and Sons, Inc.: Hoboken, N.J.; Coligan et al. eds. (2005) *Current Protocols in Protein Science,* John Wiley and Sons, Inc.: Hoboken, N.J.; and Enna et al. eds. (2005) *Current Protocols in Pharmacology,* John Wiley and Sons, Inc.: Hoboken, N.J. Abbondanzo et al. (1993) Derivation of embryonic stem cell lines. *Methods in Enzymology,* 225: 803-855; Hogan et al. (1994) *Manipulating the Mouse Embryo: A Laboratory Manual,* 2nd ed. Cold Spring Harbor Laboratory Press, Cold Spring Harbor, N.Y.

High Throughput System to Screen for and Identify Agents for the Prevention and/or Treatment of Glycogen Storage Diseases and Disorders Characterized by Accumulation of Polyglucosan High throughput screening (HTS) of libraries of compounds is an effective method for screening for agents for the prevention and/or treatment of a particular disease. However, the method is only as effective as the detection method and HTS ideally requires a cell line that can be "treated" with the compounds. While animal models are useful for screening, HTS of cells in culture allows the screening of up to 55,000 compounds. This method can be used to detect both positive and negative effects of pharmaceutical agents already FDA-approved for treatment and prevention of other diseases. Prior to the invention described herein, no such cell model existed for the accumulation of PGBs because cells simply do not accumulate glycogen.

The present invention overcomes this problem by providing a mouse model for APBD heterozygous for the GBE1 mutation and where the GBE enzyme activity was decreased enough to allow for PG accumulation (Example 1). Mouse embryonic fibroblast (MEF) cell cultures derived from this mouse were found to accumulate PGB in the cytosol, and because PG is not degradable, it accumulates and can be easily stained by the carbohydrate-specific Periodic Acid Schiff (PAS) reagent and detected by fluorescent systems that can be optimized by HTS. The results herein show that the fluorescent detection of PGBs is suitable for HTS (Examples 2 and 3) and cell density and staining have been optimized to use the HTS system to screen chemical libraries, including a variety of commercial libraries (Example 3) and the Johns Hopkins Clinical Compound Library (JHCCL) (Example 4). Any compound that either clears or decreases PGB formation in the cells has the potential to prevent and/or treat APBD, LD and other GSD and diseases and disorders characterized by the accumulation of glycogen and/or PG. Additionally, any compound that either clears or promotes PGB formation in the cells can affect blood glucose and be useful in the control of diabetes. In additions, these identified compounds can be useful tools for understanding the biochemical pathways involved in normal glycogen metabolism.

Thus, one embodiment of the present invention is a method of screening or identifying an agent for the prevention and/or treatment of a glycogen storage disease or GSD, comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for GSD. The GSDs that are included are Types I-IX.

A further embodiment of the present invention is a method of screening or identifying an agent for the prevention and/or treatment of GSD-IV comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for GSD-IV.

A further embodiment of the present invention is a method of screening or identifying an agent for the prevention and/or treatment of adult polyglucosan body disease or APBD comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for APBD.

A further embodiment of the present invention is a method of screening or identifying an agent for the prevention and/or treatment of Lanora disease or LD, comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for LD.

Yet a further embodiment of the present invention is a method of screening or identifying an agent for the prevention and/or treatment of a disease or disorder characterized by polyglucosan or PG accumulation, comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for a disease or disorder characterized by PG accumulation.

Yet a further embodiment of the present invention is a method of screening or identifying an agent for the prevention and/or treatment of a disease or disorder characterized by polyglucosan body or PGB accumulation, comprising contacting or incubating a test agent with a cell or cells derived from a mouse that is compound heterozygous for the GBE1 mutation and/or has decreased GBE activity, measuring the amount of PGB accumulation before and after contact or incubation with the agent. If the PGB accumulation clears or decreases or is lessened or reduced after contact with the test agent, the test agent is identified as a preventative and/or therapeutic agent for a disease or disorder characterized by PGB accumulation.

Yet a further embodiment of the present invention is a method of screening or identifying an agent for the prevention and/or treatment of a disease or disorder characterized by abnormal glycogen accumulation, comprising contacting or incubating a test agent with cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for a disease or disorder characterized by abnormal glycogen accumulation.

A further embodiment of the present invention is a method of screening or identifying an agent for the prevention and/or treatment of diabetes, comprising contacting or incubating a test agent with a cell or cells derived from a mouse that is compound heterozygous for the GBE1 mutation and/or has decreased GBE activity, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for diabetes.

All of the aforementioned methods can be performed using a high throughput assay or screen. Such methods are known in the art. The current invention of cells with detectable polyglucosan allows for this automation. In some embodiments, the cells are in the form of a cell line.

In some embodiments of all of these methods, the cell is a mouse embryonic cell and in further embodiments, the cell is a mouse embryonic fibroblast. In further embodiments, the cell comprises polyglucosan and/or polyglucosan bodies. In further embodiments, the PG and/or PGBs are detectable and/or measurable.

In some embodiments of all of these methods, the cell or cells are plated in multi-well plates (96-, 384-, 1536-well plates) for use in high throughput screens. In some embodiments, the cell or cells were grown and cultured for days prior to the screen. In some embodiments, the cell or cells were grown in normal growth medium and then switched to serum free medium. In some embodiments, about 1500 cells were plated in each well.

In some embodiments of all of the methods, the polyglucosan accumulation is detectable in the cell or cells. In some embodiments, the cell or cells are stained in order to detect the polyglucosan. In some embodiments, the stain is visible by light microscopy. In some embodiments, the stain is visible by fluorescent microscopy. In some embodiments, the stain allows for the detection of polysaccharides. In some embodiments, the stain is periodic acid-Schiff (PAS). In some embodiments, the stain is fluorescent.

Cells, Cell Lines and Cell Culture Systems

A further embodiment of the present invention is a cell, cells and cell line derived from a mouse that is compound heterozygous for the GBE1 mutation, designated GBE1$^{-/neo}$. This mouse is characterized by GBE enzyme activity decreased enough to allow for polyglucosan accumulation, approximately 50% of normal enzyme activity.

In certain embodiments, the cell or cells are mouse embryonic cells and in further embodiments, the cell or cells are mouse embryonic fibroblasts (MEF). In certain embodiments, the cell or cells comprise polyglucosan and/or polyglucosan bodies. In further embodiments, the PG and/or PGBs are detectable and/or measurable.

In further embodiments, the invention provides for cell lines comprising the MEF cells of the invention immortalized by methods known in the art such as by Todaro and Green 1963.

In further embodiments, the invention provides for a large number of cells that can be used at commercial scale for high throughput screens.

In further embodiments, the invention provides for a cell culture system comprising the cells or cell line of the invention, MEF cells with detectable polyglucosan, and a culture medium suitable for their growth and support.

As exemplified herein, most cell-based HTS assays are carried out in multi-well plates as they can be easily miniaturized to increase the number of wells per plate for high throughput rates, and handled with a robotic system for automation. However, any cell culture system can be used for HTS assays using the cells of the invention, including microfluidic devices for perfusion cultures and cell culture systems in a 3D environment.

Widely used HTS platforms (e.g. 96-, 384-, 1536-well plates) offer static microenvironments, with the medium supplied in a batch-wise manner. Modified multiwall plates with the integration of microfluidic systems, where the systems comprises a perfusion cell culture to compensate for liquid evaporation, can maintain a cell culture for an extended period for testing long-term effects of drugs. In addition to continuously providing nutrients and waste removal and keeping the cell culture system stable, perfusion can also be used to generate gradients of drug concentrations, as well as to create a specific physical microenvironment.

The cell of the invention can also be cultured in 3D scaffolds wherein the third dimension in the 3D scaffold provides another direction for cell-cell interactions, cell migration, and cell morphogenesis, which are critical in regulating cell cycle and tissue functions. Differences in spatial organization and distribution contribute to the difference in cell growth. In addition, 3D cell cultures provide not only the templates for cells to adhere and grow, but also the interconnectivity within the 3D constructs to allow nutrients and metabolites to be transported in and out of the engineered tissues. 3D cultures can recapitulate in vivo cellular responses to drug treatment and has potential to be a platform for drug development.

Additionally some 3D cultures can provide a 20-fold higher cellular fluorescence and significantly improve signal to noise ratio because cells are concentrated in the scaffold at the center of the well and the background fluorescence can be measured separately and subtracted to give the true live cell signal.

Mouse Model of GBE Deficiency

Additionally, described herein, is a mouse model that can be used to further screen agents and verify their activity in decreasing PGBs and preventing and treating GSD in particular APBD. This mouse model is compound heterozygous for the GBE1 mutation, and is designated GBE1$^{-/neo}$, and mimics APBD (Example 1).

Thus, one embodiment of the present invention is a method of screening or identifying an agent for the prevention and/or treatment of a GSD, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for GSD. The GSDs that are included are Types I-IX.

A further embodiment of the present invention is a method of screening or identifying an agent for the prevention and/or treatment of a GSD-IV, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for GSD-IV.

Thus, one embodiment of the present invention is a method of screening or identifying an agent for the prevention and/or treatment of APBD, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for APBD.

A further embodiment of the present invention is a method of screening or identifying an agent for the prevention and/or treatment of LD, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for LD.

Yet a further embodiment of the present invention is a method of screening or identifying an agent for the prevention and/or treatment of a disease or disorder characterized by PGB accumulation, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for a disease and/or disorder characterized by PGB accumulation.

Yet a further embodiment of the present invention is a method of screening or identifying an agent for the prevention and/or treatment of a disease or disorder characterized by abnormal glycogen accumulation, comprising contacting or incubating a test agent with a mouse that is compound heterozygous for the GBE1 mutation, measuring the amount of polyglucosan accumulation before and after contact or incubation with the agent. If the polyglucosan accumulation clears or decreases or is lessened or reduced after contact with the test agent, the test agent is identified as a preventative and/or therapeutic agent for a disease and/or disorder characterized by abnormal glycogen accumulation.

A further embodiment of the present invention is a method of screening or identifying an agent for the prevention and/or treatment of diabetes, comprising contacting or incubating a test agent with a mouse that is compound heterozygous for the GBE1 mutation, measuring the amount of polyglucosan accumulation before and after contact or incubation with the agent. If the polyglucosan accumulation clears or increases or is lessened or reduced after contact with the test agent, the test agent is identified as a preventative and/or therapeutic agent for diabetes.

Guaiacol as a Therapeutic and/or Prophylactic Agent for Glycogen Storage Disease Using this method, and the JHCCL, one compound was found to decrease polyglucosan synthesis and accumulation by 50% (Example 5). This compound was guaiacol.

After determining guaiacol decreased polyglucosan synthesis in the MEF cells of the invention, the agent was tested a mouse model of GBE deficiency, created by knocking in via homologous recombination the most common human GBE1 mutation (p.Y329S) found in Ashkenazi Jewish patients, and designated GBE1$^{ys/ys}$ (Examples 6-10). All of the guaiacol treated mice lived up to 24 months as opposed to untreated mice who started to die at about 12 months and were all dead at about 21 months (Example 10 and FIG. 9). Guaiacol did not adversely affect the animal's behavior and also had other benefits such as preventing penile prolapse seen in the disease (Example 10).

Guaiacol is a naturally occurring organic compound with the formula $C_6H_4(OH)(OCH_3)$, first isolated by Otto Unverdorben in 1826. Although it is biosynthesized by a variety of organisms, this yellowish aromatic oil is usually derived from guaiacum or wood creosote. Samples darken upon exposure to air and light. Guaiacol is present in wood smoke, resulting from the pyrolysis of lignin. The compound contributes to the flavor of many compounds, e.g., roasted coffee. Guaiacol is a precursor to various flavorants, such as eugenol and vanillin. Its derivatives are used medicinally as an expectorant, antiseptic, and local anesthetic. It also can be used as an indicator in chemical reactions that produce oxygen.

To date there are no description or suggestion that guaiacol could be effective as a prevention or treatment for APBD, GSD, LD or diseases or disorders characterized by the accumulation of PGBs.

Subjects who would benefit from administration of guaiacol would be those diagnosed with a glycogen storage disease or GSD including Types I-IX. These would include those who have not yet become symptomatic of a GSD but have been genetically tested and found to have a mutation associated with a GSD, including APBD. One such genetic test is described in PCT/US2015/063439.

Additionally, children of a parent who either have a GSD or are carriers of a mutation for GSD would be at risk for a GSD and could also benefit from the administration of guaiacol.

Additionally, persons of Ashkenazi Jewish descent could be at risk for a GSD, including APBD.

Additionally, subjects suffering from Lanora disease or LD would also benefit from the administration of guaiacol.

Additionally, subject suffering from other diseases and/or disorders with hallmark histopathology of the accumulation of glycogen or PG or PG bodies would also benefit from the administration of guaiacol.

Additionally, subject suffering from diabetes would also benefit from the administration of guaiacol.

Pharmaceutical Compositions and Methods of Administration

The present invention encompasses the administration of guaiacol. Preferred methods of administration include oral; mucosal, such as nasal, sublingual, vaginal, buccal, or rectal; parenteral, such as subcutaneous, intravenous, bolus injection, intramuscular, or intra-arterial; or transdermal administration, to a subject. Thus, the guaiacol must be in the appropriate form for administration of choice. A preferred dosage form is oral.

Such compositions for administration may comprise a therapeutically effective amount of the guaiacol and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for parenteral administration include aqueous and non-aqueous sterile injectable solutions or suspensions, which may contain anti-oxidants, buffers, baceriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

A preferred therapeutically effective dose of guaiacol ranges from about 6 mg/kg to 720 mg/kg. A further preferred dose ranges from 6 mg/kg to 12 mg/kg. A further preferred dose ranges from 6 mg/kg to 22.5 mg/kg. A further preferred dose ranges from 6 mg/kg to 45 mg/kg. A further preferred dose ranges from about 22.5 mg/kg to about 45 mg/kg. A further preferred dose ranges from about 22.5 mg/kg to about 90 mg/kg. A further preferred dose ranges from about 22.5 mg/kg to about 180 mg/kg. A further preferred dose ranges from about 22.5 mg/kg to about 360 mg/kg. A further preferred dose ranges from about 45 mg/kg to about 90 mg/kg. A further preferred dose ranges from about 45 mg/kg to about 180 mg/kg. A further preferred dose ranges from about 45 mg/kg to about 360 mg/kg.

Administration of guaiacol can be once a day, twice a day, three times a day, four times a day, five times a day, up to six times a day, preferably at regular intervals. For example, when the guaiacol is administered four times daily, doses would be at 8:00 AM, 12:00 PM, 4:00 PM, and 8:00 PM.

A preferred dosage form is oral. The guaiacol can be suspended in water for oral administration.

Doses can be adjusted to optimize the effects in the subject. For example, the guaiacol can be administered at a lower dosage to start such as 22.5 mg/kg and then increased over time to 45 mg/kg, to 90 mg/kg, to 180 mg/kg, to 360 mg/kg, up to 720 mg/kg, depending upon the subject's response. A subject can be monitored for improvement of their condition prior to increasing the dosage.

EXAMPLES

The present invention may be better understood by reference to the following non-limiting examples, which are presented in order to more fully illustrate the preferred embodiments of the invention. They should in no way be construed to limit the broad scope of the invention.

Example 1—Generation of Mouse Model for GBE Deficiency

Two alleles of the Gbe1 locus were generated, a complete null deletion Gbe1$^{-/-}$, and a hypomorphic neomycin cassette insertion mutation Gbe1$^{neo/neo}$. Deletion of exon 7 resulted in a model of fetal Andersen disease, while inserting the neomycin cassette downstream of exon 7 resulted in an adult form of the disease, APBD. The null and hypomorphic mutations were created using FRT recombination consensus sequences upstream and downstream of the mouse Gbe1 exon 7 via homologous recombination (FIG. 1). Gbe1$^{+/neo}$ animals were intercrossed to generate Gbe1$^{neo/neo}$ mice, or were bred to a Flpe-expressing mice strain (GT (ROSA)$^{26Sor-Flpe}$) in order to delete the sequences between the two FRT sites (represented by the yellow band in FIG. 1A), thus generating the null allele. The heterozygous exon 7 deleted mice (Gbe1$^{+/-}$) were interbred to obtain homozygous animals Gbe1$^{-/-}$.

To confirm the absence of exon 7, total muscle RNA was isolated from newborn litters of Gbe1$^{+/-}$ parents and amplified by RT-PCR analysis. In mice harboring the FLPe-mediated deletion, a 210 bp long fragment corresponding to exon 7 was absent from the cDNA. RT-PCR products were sequenced to demonstrate the exact location of the deletion (FIG. 1B). See Akman et al. 2011.

Example 2—Generation of Mouse Embryonic Cells from the Gbe1 Deficient Mice with Detectable Polyglucosan Bodies Mouse embryonic cell lines (MEF) from wild type (Gbe1$^{+/+}$) and Gbe1$^{neo/-}$ mice were generated. The Gbe1$^{neo/-}$ cell line had 7.5%±5 of normal GBE activity, about half the GBE activity present in white blood cells from APBD patients. This low level of enzyme activity is achieved by breeding heterozygous exon 7-deleted mice with Gbe1$^{neo/neo}$ mice and generating compound heterozygous offspring (Example 1).

Skin fibroblasts from wild type or Gbe1$^{neo/-}$ E17.5 embryos were cultured to establish the MEF cell line by methods known in the art (FIG. 2). Diastase-resistant PAS positive staining was used specifically for carbohydrate staining. After paraformaldehyde fixation, cells were washed with PBS and normal glycogen was degraded by alpha-amylase digestion. The residual polysaccharides and PG in MEF were treated with periodic acid to oxidize sugars to aldehydes, which react with the Schiff reagent and stain pink. Although PAS staining was very efficient to detect PG (see FIGS. 2A, 2B, 2C, 2E, and 2G), the IN Cell 2000 cell detection system relies on fluorescence staining. PAS staining itself is fluorescent due to pararosanilin reagents, such as Rhodamine and TRITC, which can be excited (400 nm) and emits light detectable in red range (510 nm) (FIGS. 2D, 2F and 2H).

Example 3—Automated Detection System Set Up

High throughput screening (HTS) depends on a reliable detection system capable of showing clearly the effect of treatment on the cells under study. Because PGBs were readily detectable by PAS staining either with light microscopy or with fluorescent microscopy in the cell line derived from GBE-deficient mice, this detection method was adapted to an automated high throughput screening system.

To set up the automated detection system, control Gbe1$^{+/+}$ and Gbe1$^{neo/-}$ MEFs were plated at different density on 384-well plates in order to obtain optimal cell density. A second important optimization regarded the diastase digestion of normal glycogen, keeping in mind that PGBs are resistant to diastase digestion and longer incubation times and/or higher enzyme concentrations are needed to digest PG. These optimizations were performed by adjusting digestion time and α-amylase concentration. After optimizing digestion and staining, MEFs were grown on 384-well plates in the same incubator that were used for treatments, Cell:: Explorer (Perkin Elmer). Semi-confluent cells were grown in reduced serum media for three days with Rapamycin (10, 20, 40 and 80 nM), high glucose (25 mM), and ketogenic glucose-free media (Santra et al. 2004). After three days, the cells were washed with phosphate buffered saline and fixed in 4% paraformaldehyde. After diastase digestion, they were stained with PAS, and, after brief nuclear staining with Hoechst, the plates were analyzed by IN Cell 2000, GE Healthcare (Piscataway, N.J.), a high-throughput imaging system capable of performing high-content analysis using a wide array of micro plates. The instrument was equipped with large CCD camera (resolution 2048×2048 pixels), allowing whole-well imaging in 384-well micro plates. IN Cell 2000 has several imaging modes, including image restoration and deconvolution to obtain confocal-like quality with high throughput. In this initial set up, concentrations of Rapamycin 2 and 4 times higher than normal were used in order to assess toxicity and cell death. Automated quantitative results were obtained in terms of relative fluorescence per cell. Relative fluorescence per positive cells were analyzed and its significance were determined by z score according to plate average or by B score if there is a positional effect related to row and column that occurs in multi well plate cell cultures (Brideau et al. 2003).

Example 4—Screening of a Compound Library Using HTS of the MEF Cells

Materials and Methods

Using the cells of Example 2 in the HTS format of Example 3, the John Hopkins University Clinical Compound Library (JHCCL containing 1,700 compounds) was screened at the Columbia University HTS core facility.

1500 cells were plated per well to 384-well plates. Cells were grown in their normal growth medium. On day two, the medium was switched to serum free medium. On day three, the cells were treated with the compounds. After three days, the medium was removed and the cells were fixed in 4% formaldehyde in PBS overnight at 4° C. The following day the cells were stained and analyzed as set forth in Example 3.

Results

One hit was obtained corresponding to a compound that decreased polyglucosan synthesis more than 50% at 6.75 µM concentration (FIG. 3). Subsequent experiments showed that this inhibition is either at the level of glycogen synthesis or at the level of glucose import into the cell, because this compound also decreased glycogen content in HepG2 liver epithelial cell line cultured in Dulbecco's modified eagle media supplemented with 150 µM of cobalt chloride (results not shown). Cobalt chloride activates glucose import and glycogen synthesis: in its absence, the MEF cells do not accumulate enough glycogen to be detected biochemically. This compound identified was guaiacol and has been used as an expectorant and flavoring food additive but is no longer being marketed for medical purposes.

Example 5—Guaiacol Increases the Phosphorylation of Glycogen Synthase

Glycogen synthase is an allosteric enzyme that can be activated by glucose 6 phosphate or inactivated by phosphorylation of a serine residue on the enzyme. Thus, the phosphorylation status of GYS1 in muscle extracts which is the indicator of glycogen synthase activity was determined.

Wild type mice were administered guaiacol suspended in water at concentrations of 45, 90, 180, 360, and 720 mg/kg. Two hours after administration, muscle extracts were obtained and Western blot analysis of GYS1 was performed.

Figure 4:
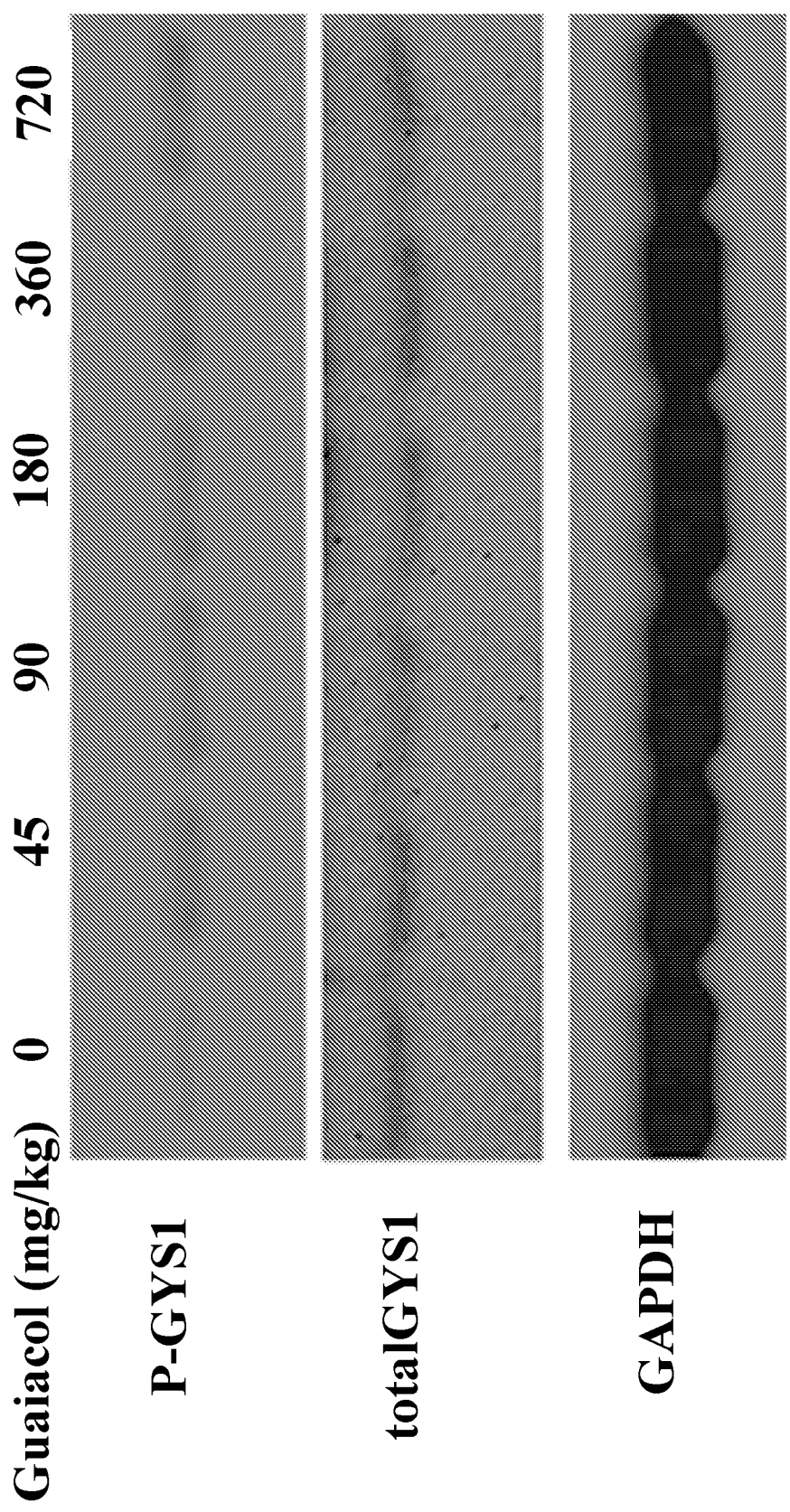
FIG. 4 is a Western blot of GYS1 and GAPDH in muscle extracts obtained from wild type mice two hours after administration with guaiacol, suspended in water, in the indicated dosage amounts on the top panel by oral gavage.

FIG. 4 shows the phosphorylation of GYS1 increased with guaiacol treatment compared to total GYS1 protein. Protein loading was monitored by the housekeeping gene GAPDH.

Since the effect of guaiacol suddenly increased the phosphorylation of GYS1, lower concentrations were tested at 6, 12, 22.5 and 45 mg/kg and it was found that 22.5 mg/kg was the lowest guaiacol concentration can be given in drinking water.

Example 6—Effect of Guaiacol Treatment on Tissue Glycogen Content

A mouse model of GBE deficiency created by knocking in via homologous recombination the most common human GBE1 mutation (p.Y329S) found in Ashkenazi Jewish patients has been developed by the inventors and designated Gbe1$^{ys/ys}$ (Akman et al. 2015).

After one month of treatment, four mice from each group (untreated wild type and Gbe1$^{ys/ys}$ mice and guaiacol-treated wild type and Gbe1$^{ys/ys}$ mice) were sacrificed and tissue glycogen contents were measured as described by Pederson et al. 2004.

Figure 5:
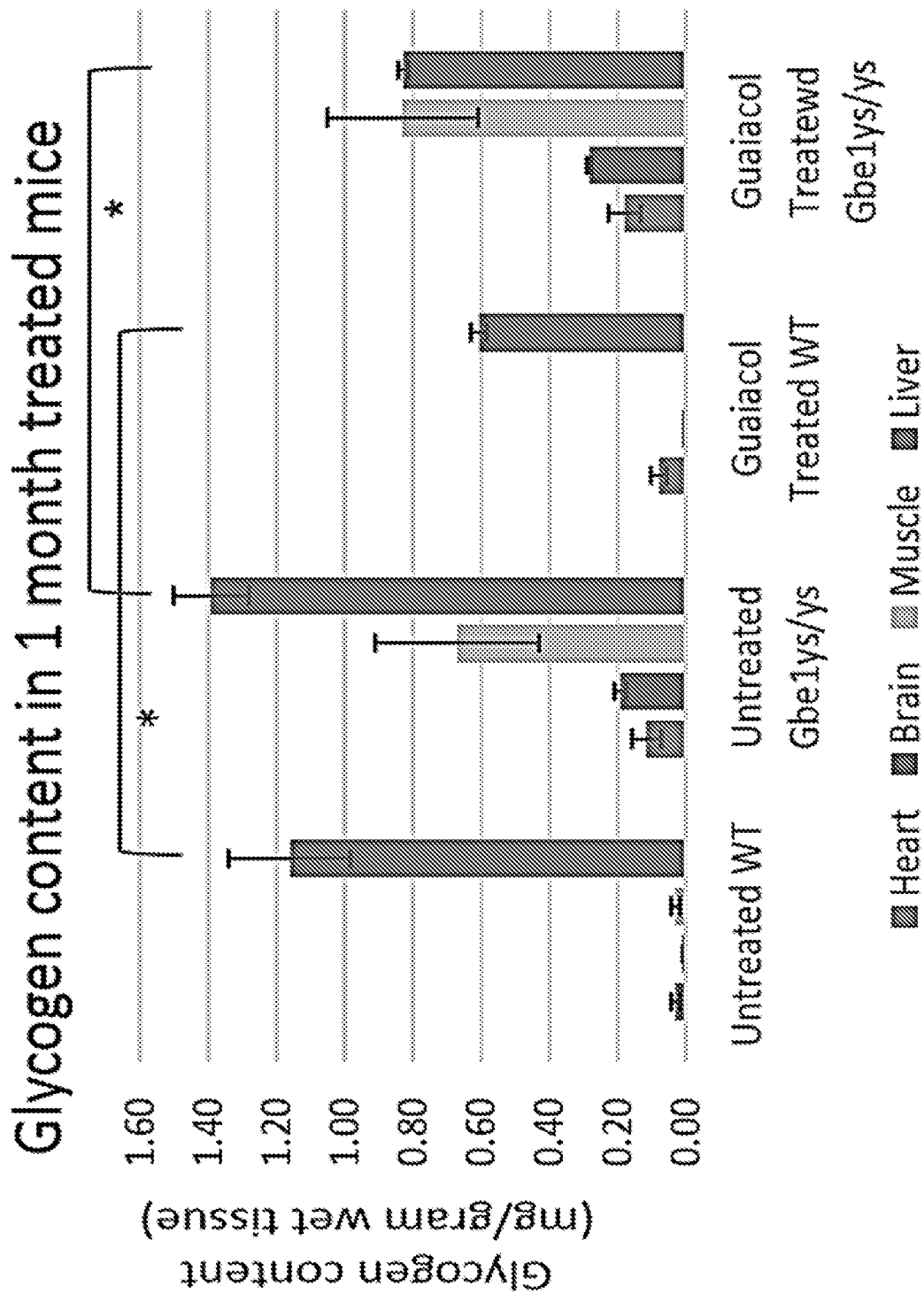
FIG. 5 is a graph depicting the results of heart, brain, muscle and liver glycogen content in wild type and Gbe1$^{ys/ys}$ mice, and guaiacol-treated wild-type and Gbe1$^{ys/ys}$ mice. Glycogen was measured after a 16 hour fast (n=4 for each treatment). Glycogen content is expressed as percent glucose mg/gram fresh tissue. Error bars represent the mean±SD, $P<0.001$ where indicated (*).

A significant decrease in glycogen content of the liver was observed but the glycogen content in brain heart and muscle did not change (FIG. 5). In the later treatments, glycogen content in the brain and muscle of treated mice showed slight increase compared to untreated Gbe1$^{ys/ys}$ mice.

Example 7—Liver is More Responsive to Guaiacol than Other Tissues

Because the treatment with guaiacol decreased the glycogen in liver but actually increased it in brain, muscle and heart, a glucose tolerance test was performed on the mice.

Figure 6:
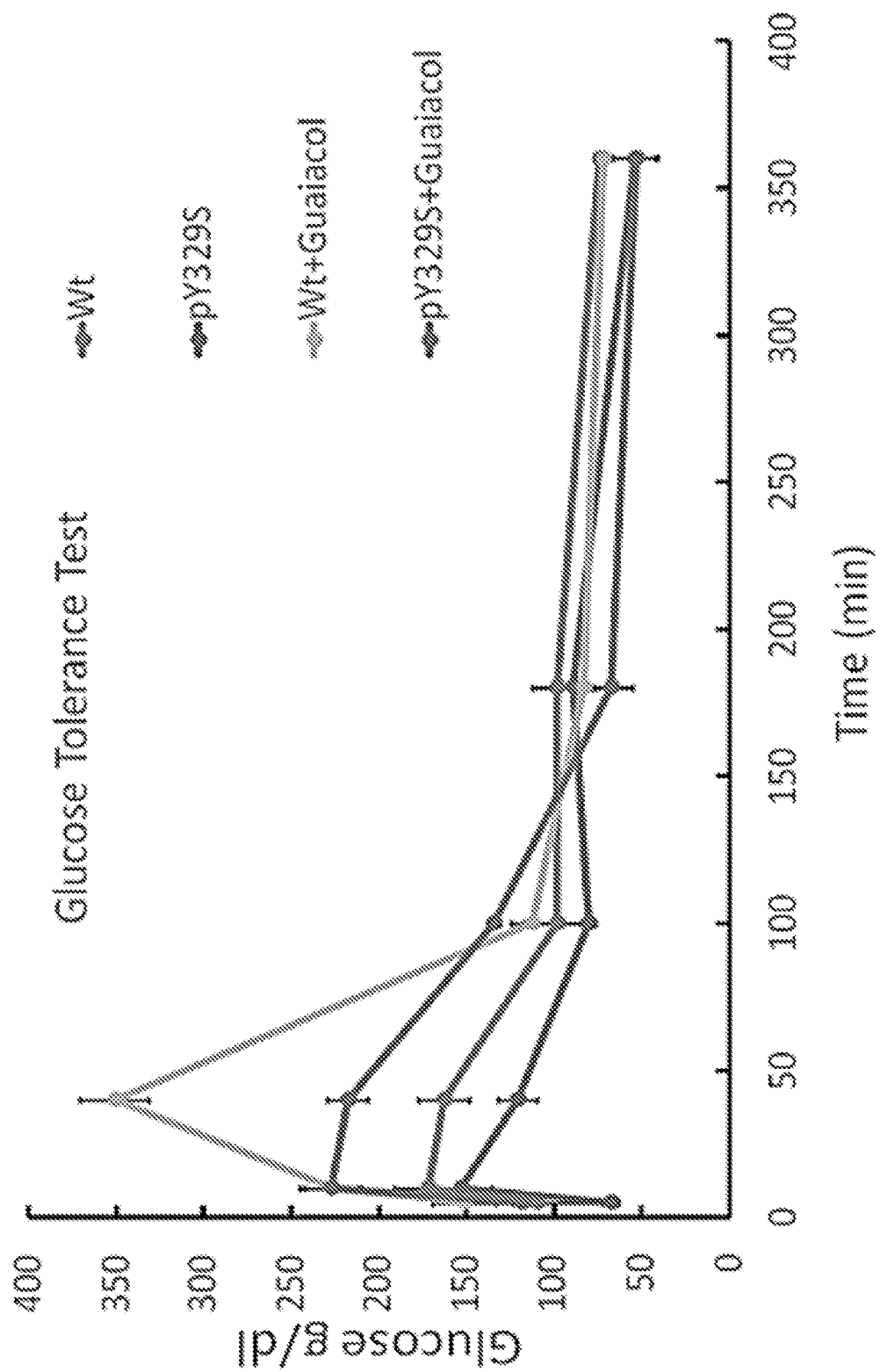
FIG. 6 is a graph showing that guaiacol increases blood glucose concentration. Blood glucose content was measured at times indicated in guaiacol-treated and untreated wild type and APBD (p.Y329s) mice. n=3 in each group.

After overnight fasting, mice were injected glucose and the blood glucose levels were measured. As shown in FIG. 6, the guaiacol-treated mice had higher blood glucose and it remained high longer than the control mice.

This explains why glycogen increases in the other tissues although GYS1 and 2 are inhibited by phosphorylation. Glucose 6 phosphate is an avid activator of GYS1 or 2 and high glucose concentration overrides the phosphorylation-mediated inhibition and initiates the glycogen synthesis.

Example 8—Guaiacol Treatment Increases Phosphorylation of AMP kinase

Figure 7:
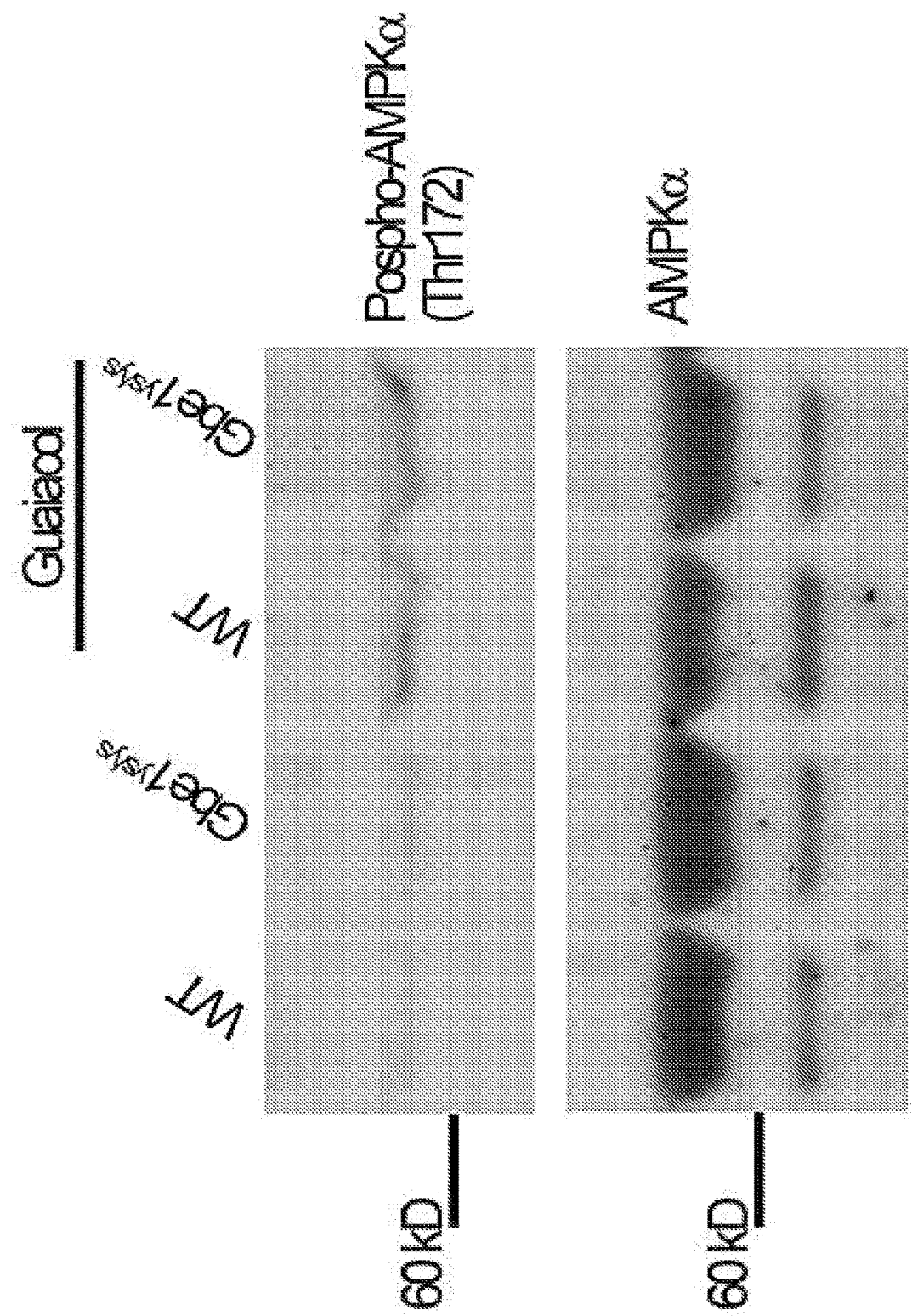
FIG. 7 is a Western blot of phospho AMPK-α and total AMPK in muscle extracts obtained from wild type and Gbe1$^{ys/ys}$ mice, and guaiacol-treated wild type and Gbe1$^{ys/ys}$ mice.

Glycogen synthesis and breakdown is regulated according to the energy state of the cell. When glucose is abundant amount of ATP is high and AMP kinase remains un-phosphorylated. However when glucose concentrations go down so do the ATP levels because it is being converted to ADP and AMP. Higher concentrations of ADP and AMP activates AMP kinase alpha (AMPK-α, (Suter et al. 2006). In turn, active AMPK-α triggers the catabolic metabolism preventing the synthesis of glycogen, lipids and most of the proteins while activating glycogen breakdown oxidative phosphorylation and mitochondrial biogenesis. Therefore the state of AMP kinase phosphorylation in the liver extracts was tested and as shown in FIG. 7, guaiacol treatment increased Thr 172 phosphorylation of AMP kinase, which is the indicator of its activation. Total AMPK-α protein estimates the relative phosphorylation (FIG. 7).

Example 9—Mechanism of AMPK-α Activation

Figure 8:
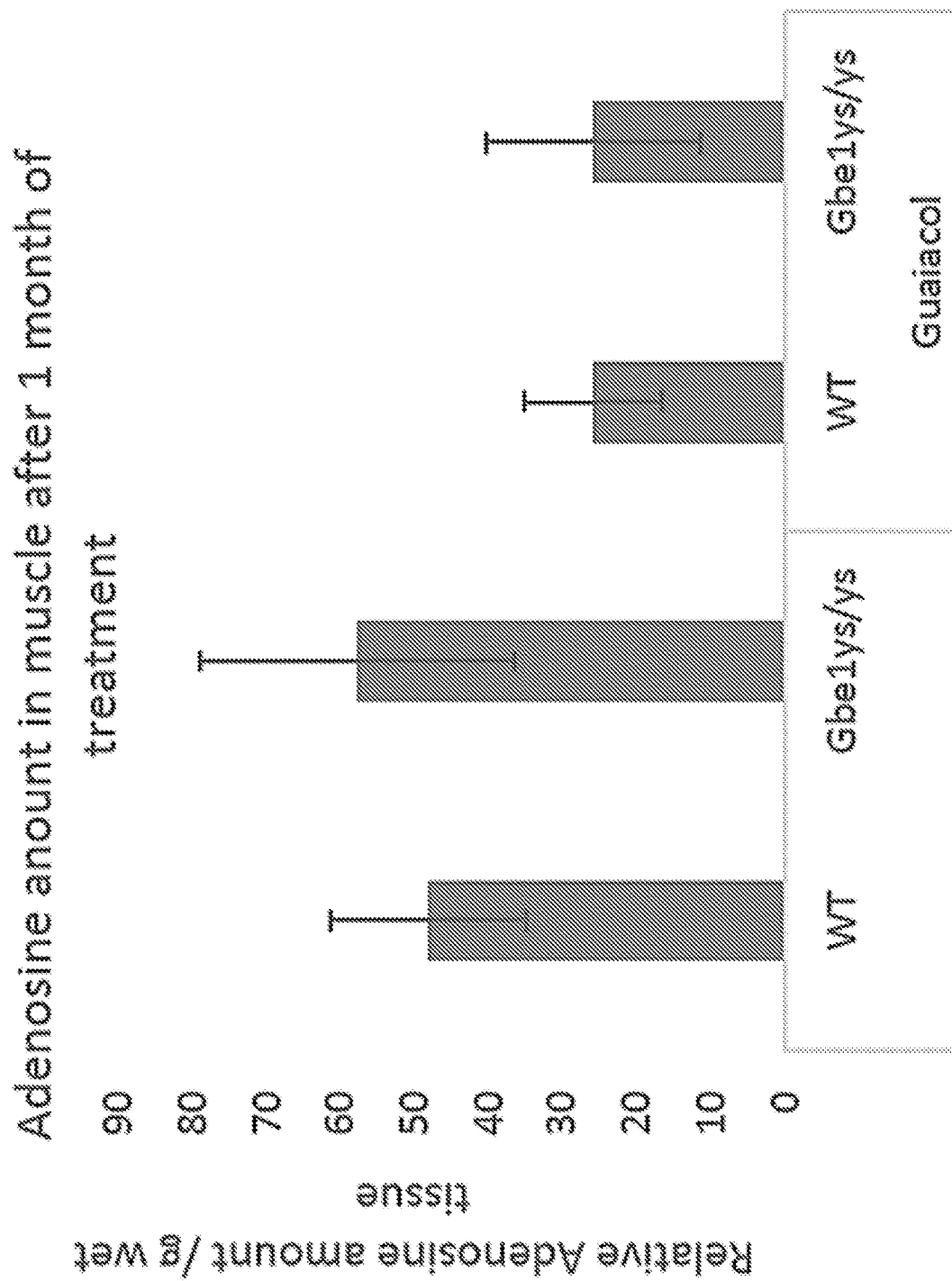
FIG. 8 is a graph depicting results of high performance liquid chromatography analysis of adenosine in muscle of wild type and Gbe1$^{ys/ys}$ mice, and guaiacol-treated wild type and Gbe1$^{ys/ys}$ mice.

AMPK-α has 3 subunits, the heterotrimeric protein AMPK is formed by α, β, and γ subunits. Each of these three subunits takes on a specific role in both the stability and activity of AMPK. (Stapleton et al. 1996). Specifically, the γ subunit includes four particular cystathionine beta synthase (CBS) domains giving AMPK its ability to sensitively detect shifts in the AMP: ATP ratio. The four CBS domains create two binding sites for AMP commonly referred to as Bateman domains. Binding of one AMP to a Bateman domain cooperatively increases the binding affinity of the second AMP to the other Bateman domain (Akman et al. 2007). Since the concentrations of AMP versus ATP can activate AMPK-α, AMP, ADP and ATP levels were measured in muscle extracts, although there was no significant difference between wild type or Gbe1$^{ys/ys}$ and guaiacol-treated wild type or Gbe1$^{ys/ys}$ mice, there was a significant decrease in adenosine levels in mice treated with guaiacol (53%+/−27.5 in wild-type and 48%+/−36.8 in Gbe1$^{ys/ys}$ (n=4 in each group and p<0.02 and 0.03 respectively) (FIG. 8).

Example 10—Guaiacol Increases Lifespan of the Mice with p.Y329S Mutation

Mice were treated with guaiacol in drinking water for 12 months every other day by preparing fresh guaiacol solution in water (3.8 g/liter or 3.1 ml/liter) considering the fact that an adult mouse drinks 6 ml water every day (Bachamov et al. 2002).

22.5 mg/kg of guaiacol did not adversely affect the animal behavior, as concluded by grip tests and weight gain or loss which the same in both groups.

Figure 9:
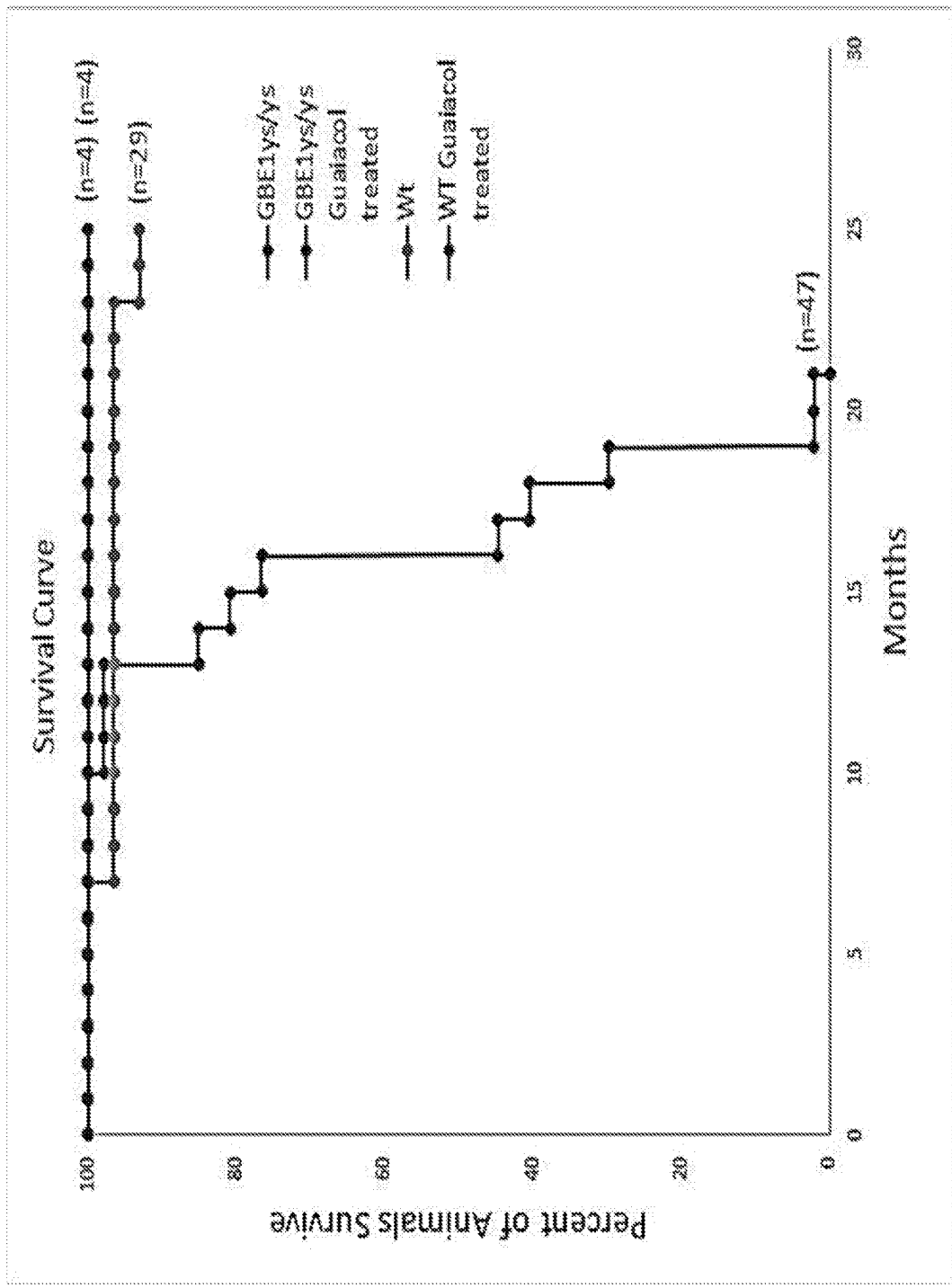
FIG. 9 is a Kaplan-Meier plot which illustrates the incidence of death in Gbe1$^{ys/ys}$ (n=47), versus wild type mice (n=29), and guaiacol-treated Gbe1$^{ys/ys}$ and wild type mice (n=4 each).

Treated Gbe1$^{ys/ys}$ mice lived up to 24 months at time they were sacrificed as required by the protocol (FIG. 9).

One obvious benefit of the guaiacol treatment in male mice is that they did not have penile prolapse, a condition observed in untreated mice starting at age as early as 1 year. Although treated mice lived longer, they had spastic gait and slightly higher polyglucosan in the muscle brain and heart. Although guaiacol treatment decreased PG content in the liver, this tissue-specific inhibition of glycogen synthase cannot explain the increase in life span and correction of penile prolapse. This suggests that polyglucosan in APBD has another toxic function that was partially prevented by guaiacol treatment.

REFERENCES

Akman et al. *Pediatr. Res.* 2007. 62(4):499-504
Akman et al. *Hum. Mol. Genet.*, August 2011. 20(22):4430-39
Akman et al. *Hum. Mol. Genet.* September 2015. 24(23): 6801-10
Andersen, *Lab. Invest.* 1956. 5(1):11-20
Bachmanov et al. *Behav. Genet.*, 2002. 32(6):435-43
Brideau et al. *J. Biomol. Screen*, 2003. 8(6):634-47
Bruno et al. *Ann. Neurol.*, 1993. 33(1):88-93
Chan et al. *Neurology,* 2004. 63(3):565-7
Deutsch and Young, *Pediatr. Dev. Pathol.,* 2009. 12(6):475-80
Ianzano et al. *Hum. Mutat.*, 2005. 26(4):397
Illingworth et al. *J. Biol. Chem.*, 1952. 199(2):631-40
Jiang et al. *J. Biol. Chem.*, 2010. 285(45):34960-71
Klein, *Gene Reviews*, Apr. 2, 2009

Malfatti et al. *Ann. Neurol.*, December 2014, 76(6):891-8
Marquez et al. *Vet. J.*, 2010. 183(2):222-5
Meng et al. *Neuropathology*, 2009. 29(6):664-71
Minassian et al. *Nat. Genet.*, 1998. 20(2):171-4
Mochel et al. *Ann. Neurol.*, September 2012 72(3):433-441
Nilsson et al. *Ann. Neurol.*, December 2013 74(6):914-9
Pederson et al. *Mol. Cell. Biol.,* 2004. 24(16):7179-87
Santra et al. *Ann Neurol.,* 2004. 56(5):662-9.
Skurat et al. *J. Biol. Chem.,* 2002. 277(22): p. 19331-8
Stapleton et al. *J. Biol. Chem.,* 1996. 271(2):611
Suter et al. *J. Biol. Chem.,* 2006. 281: 32207-16
Todaro and Green *J. Cell. Biol.* 1963. 17:299-313
Tonin et al. *Neuromuscul. Disord.,* 1992. 2(5-6):419-22
Turnbull et al. *PLoS Genet.,* 2011. 7(4):e1002037
Wu et al. *Mol. Genet. Genomics,* 2001. 265(4): p. 622-35
Zhai et al., *Gene,* 2000. 242(1-2):229-35

The invention claimed is:

1. A method for ameliorating a disease or a disorder characterized by polyglucosan accumulation or abnormal glycogen accumulation, wherein said disease or disorder is selected from the group consisting of types I-IX glycogen storage disease, adult polyglucosan body disease (APBD), and Lafora disease in a subject in need thereof, the method comprising administering to said subject a therapeutically effective amount of guaiacol.

2. The method of claim 1, wherein the disease is a type IV glycogen storage disease.

3. The method of claim 1, wherein the disease is APBD.

4. The method of claim 1, wherein the subject in human.

5. The method of claim 1, wherein the guaiacol is administered orally.

6. The method of claim 1, wherein the guaiacol is administered in a dosage from about 22.5 to 45 milligrams of guaiacol per kilogram of the subject.

7. The method of claim 1, wherein the guaiacol is administered in a dosage from about 22.5 to 180 milligrams of guaiacol per kilogram of the subject.

8. The method of claim 1, wherein the guaiacol is administered in a dosage from about 22.5 to 720 milligrams of guaiacol per kilogram of the subject.

9. A method for inhibiting at least one of glycogen synthase (GYS) 1 and GYS2 in a subject afflicted with a disease or a disorder characterized by polyglucosan accumulation or abnormal glycogen accumulation, the method comprises administering to said subject an effective amount of guaiacol, thereby inhibiting at least one of GYS1 and GYS2 in the subject afflicted with a disease or a disorder characterized by polyglucosan accumulation or abnormal glycogen accumulation.

10. The method of claim 9, wherein said disease or disorder characterized by polyglucosan accumulation or abnormal glycogen accumulation is selected from the group consisting of: types I-IX glycogen storage disease, adult polyglucosan body disease (APBD), and Lafora disease.

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: Mus musculus

<400> SEQUENCE: 1

Ala Ser Ser Arg Tyr Ser Ser Trp Glu Val
1               5                   10

<210> SEQ ID NO 2
<211> LENGTH: 26
<212> TYPE: DNA
<213> ORGANISM: Mus musculus

<400> SEQUENCE: 2
cttcaagtcg ttaccagctg ggaagt                                    26

<210> SEQ ID NO 3
<211> LENGTH: 12
<212> TYPE: PRT
<213> ORGANISM: Mus musculus

<400> SEQUENCE: 3

Phe Phe Ala Ala Ser Ser Trp Glu Val Leu Arg Phe
1               5                   10

<210> SEQ ID NO 4
<211> LENGTH: 37
<212> TYPE: DNA
<213> ORGANISM: Mus musculus

<400> SEQUENCE: 4 ctttttttgca gcttcaagct gggaagtttt aagattc                       37